(12) United States Patent
Kendrick

(10) Patent No.: US 8,960,727 B2
(45) Date of Patent: Feb. 24, 2015

(54) METHOD AND SYSTEM FOR VISUALLY INDICATING A SECURE CONNECTION

(75) Inventor: Paul A. Kendrick, Totowa, NJ (US)

(73) Assignee: Carefusion Corporation, San Diego, CA (US)

( * ) Notice: Subject to any disclaimer, the term of this patent is extended or adjusted under 35 U.S.C. 154(b) by 360 days.

(21) Appl. No.: 12/984,007

(22) Filed: Jan. 4, 2011

(65) Prior Publication Data
US 2012/0169044 A1    Jul. 5, 2012

(51) Int. Cl.
*F16L 37/00*   (2006.01)
*A61M 39/10*   (2006.01)
*A61M 16/08*   (2006.01)
*A61M 16/01*   (2006.01)

(52) U.S. Cl.
CPC ....... *A61M 39/1011* (2013.01); *A61M 16/0816* (2013.01); *A61M 16/01* (2013.01); *A61M 2039/1033* (2013.01); *A61M 2039/1044* (2013.01); *A61M 2205/58* (2013.01); *A61M 2205/583* (2013.01); *A61M 2205/584* (2013.01)
USPC .......................................................... 285/93

(58) Field of Classification Search
USPC ........... 285/93, 360, 376, 401, 402, 361, 396, 285/316
See application file for complete search history.

(56) References Cited

U.S. PATENT DOCUMENTS

| | | | | |
|---|---|---|---|---|
| 423,323 A | * | 3/1890 | Johnson | 285/100 |
| 1,130,726 A | * | 3/1915 | Greve | 285/376 |
| 1,847,379 A | * | 3/1932 | Buchet | 285/316 |
| 2,076,918 A | * | 4/1937 | Robison | 285/82 |
| 3,687,137 A | * | 8/1972 | Johnson | 128/204.13 |
| 5,741,084 A | * | 4/1998 | Del Rio et al. | 403/349 |
| 6,585,016 B1 | | 7/2003 | Falligant et al. | |
| 6,929,041 B2 | | 8/2005 | Falligant et al. | |
| 7,168,467 B2 | | 1/2007 | Turker et al. | |
| 7,287,561 B2 | | 10/2007 | Turker et al. | |
| 7,389,801 B2 | | 6/2008 | Turker et al. | |
| 7,490,607 B2 | | 2/2009 | Bottom et al. | |

* cited by examiner

*Primary Examiner* — Daniel P Stodola
*Assistant Examiner* — James Linford
(74) *Attorney, Agent, or Firm* — McDermott Will & Emery LLP

(57) ABSTRACT

A connector arrangement for attaching a gas conduit to a gas supply device and visually indicating the proper connection between the two components. The connector arrangement includes a connector attached to a gas conduit and a receptacle formed on a gas supply device. A visual indicator is associated with the receptacle such that when the connector is properly received within the receptacle, the visual indicator provides a visual indication to the user that the connection has been made. The visual indicator can include two distinct colors that provide a visual indication of whether a proper connection has been made. The visual indicator could alternatively include a light that is illuminated when the proper connection is made.

13 Claims, 13 Drawing Sheets

METHOD AND SYSTEM FOR VISUALLY INDICATING A SECURE CONNECTION

BACKGROUND OF THE INVENTION

The present disclosure generally relates to a connector arrangement for attaching a gas conduit to a gas supply device. More specifically, the present disclosure relates to a connector arrangement that visually indicates a secure connection between the gas conduit and the gas supply device, such as an anesthesia machine.

Presently, many different types of connection arrangements are available for joining a gas conduit to a gas supply device. These types of connector arrangements typically include some type of attachment arrangement that secures a connector on the gas conduit to a receptacle of the gas supply device to prevent inadvertent disconnection of the two components. However, it is oftentimes difficult to determine whether a secure connection has been made without either physically pulling on the gas conduit or visually examining the orientation of the connector and the receptacle.

A secure connection between a patient circuit and an anesthesia machine is critical to insure that the proper amount of anesthetic agent is being delivered to the patient and not being dispersed into the environment surrounding the patient. Therefore, a need exists to insure a secure connection between the gas conduit and the anesthesia machine to facilitate the proper connection of the two components.

SUMMARY OF THE INVENTION

The present disclosure relates to a connector arrangement that allows a gas conduit to be joined to a gas supply device. The connector arrangement of the present disclosure visually indicates when a secure connection is made between the gas conduit and the gas supply device. Further, the connector arrangement also visually indicates when no connection is present between the gas conduit and the gas supply device.

The connector arrangement generally includes a connector that is attached to the gas conduit. The connector includes a locking arrangement that allows the connector to be securely connected to a receptacle formed on the gas supply device. The receptacle formed on the gas supply device includes a receiving arrangement that interacts with the locking arrangement on the connector to positively retain the connector within the receptacle. The interaction between the locking arrangement on the connector and the receiving arrangement on the receptacle prevent inadvertent separation of the gas conduit and the gas supply device.

The connector arrangement further includes a visual indicator that is associated with the receptacle. The visual indicator provides a visual indication of when the connector is securely received within the receptacle. Additionally, the visual indicator can provide a visual indication of when the connector is not received within the receptacle. The visual indicator allows a user to visually determine whether a proper connection has been made between the gas conduit and the gas supply device.

In one embodiment of the disclosure, the visual indicator is an indicator light that is illuminated when the connector is securely received in the receptacle. In this embodiment, the indicator light is connected to an activation switch formed in the receptacle. When the connector is received within the receptacle, the activation switch is closed to provide power to the illumination light. In one embodiment, the illumination light is an LED.

In another alternate embodiment, the visual indicator is a visual indicator shroud that is position within the receptacle. The visual indicator shroud includes both a first portion and a second portion that have different colors. As an illustrative example, the first portion is colored red and the second portion is colored green.

When the connector is not properly received within the receptacle, a first portion of the indicator shroud is visible. The red color of the first portion indicates to a user that a proper connection has not been made.

When the connector is properly received within the receptacle, a second, green portion of the indicator shroud is visible to the user. The second, green color visible to the user indicates that the connector is positively retained within the receptacle.

In each embodiment of the disclosure, the connector arrangement includes some type of visual indicator that provides the user with a visual indication of when the connector is securely received in the receptacle. The visual indication allows a user to quickly and easily determine whether a proper connection has been made between the gas conduit and the gas supply device. In one embodiment, the connection is formed between and anesthesia machine and a patient breathing circuit. However, other implementations of the connector arrangement are contemplated as being within the scope of the disclosure.

BRIEF DESCRIPTION OF THE DRAWINGS

The drawings illustrate the best mode presently contemplated of carrying out the disclosure. In the drawings.

DETAILED DESCRIPTION

Figure 1:
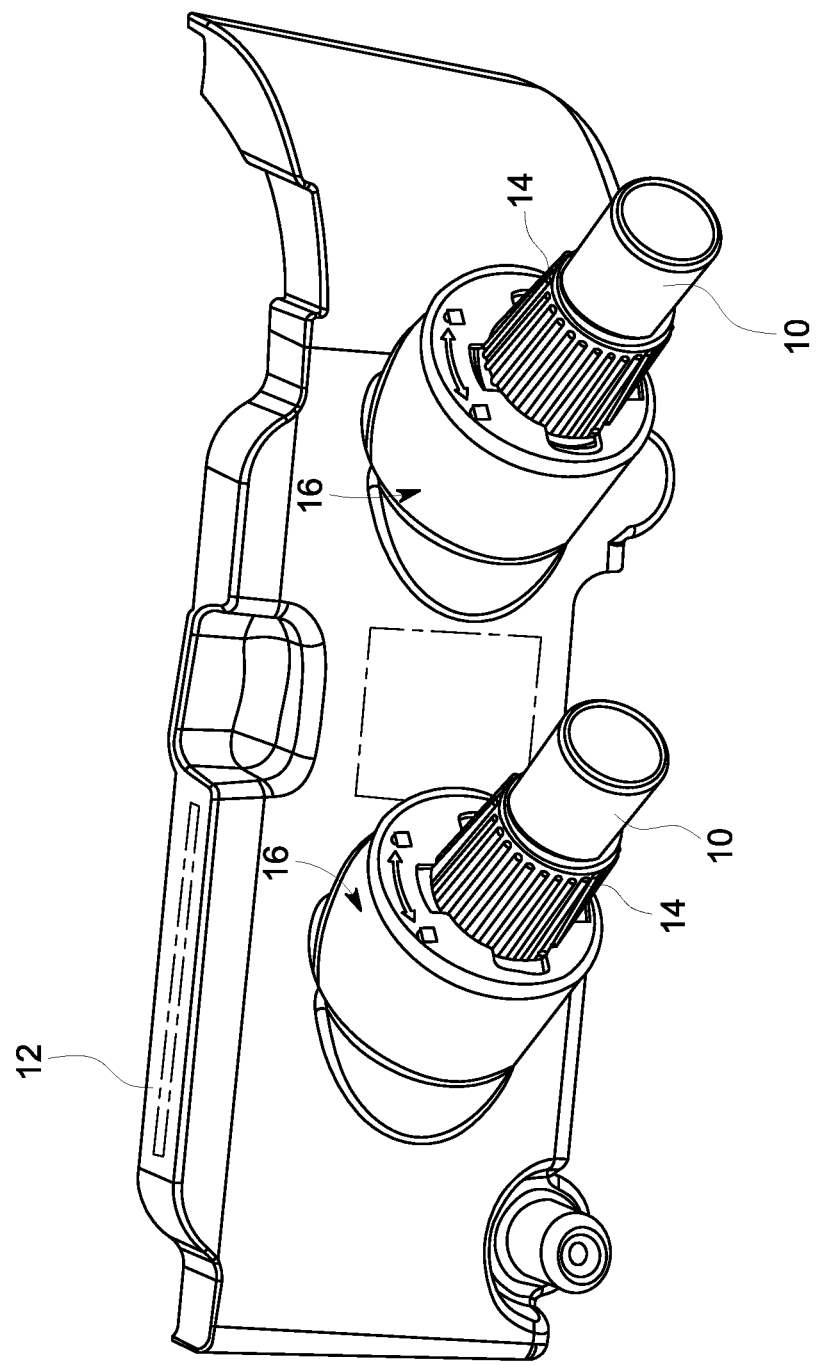
FIG. 1 is a perspective view of the connection between two gas conduits of a patient breathing circuit and an anesthesia machine.

FIG. 1 illustrates the connection between a pair of gas conduits 10 and a gas supply device, such as an anesthesia machine 12. Although the anesthesia machine 12 is shown in the embodiment of FIG. 1 as the gas supply device, it should be understood that the connector arrangement of the present disclosure could be utilized between gas conduits and various other types of gas supply devices other than an anesthesia machine 12.

In the embodiment shown in FIG. 1, each of the gas conduits 10 includes a connector 14 securely attached to one end of the gas conduit 10. Each of the gas conduits 10 is connected to a receptacle 16 formed on the anesthesia machine 12. The interaction between the connector 14 on the gas conduit 10 and the receptacle 16 allows gas to be delivered between the anesthesia machine 12 and the respective gas conduit 10. In the embodiment illustrated in FIG. 1, the gas conduits 10 form part of a patient circuit that delivers an anesthetic agent to a patient and receives exhalation gases from the patient during a normal breathing cycle.

Figure 2:
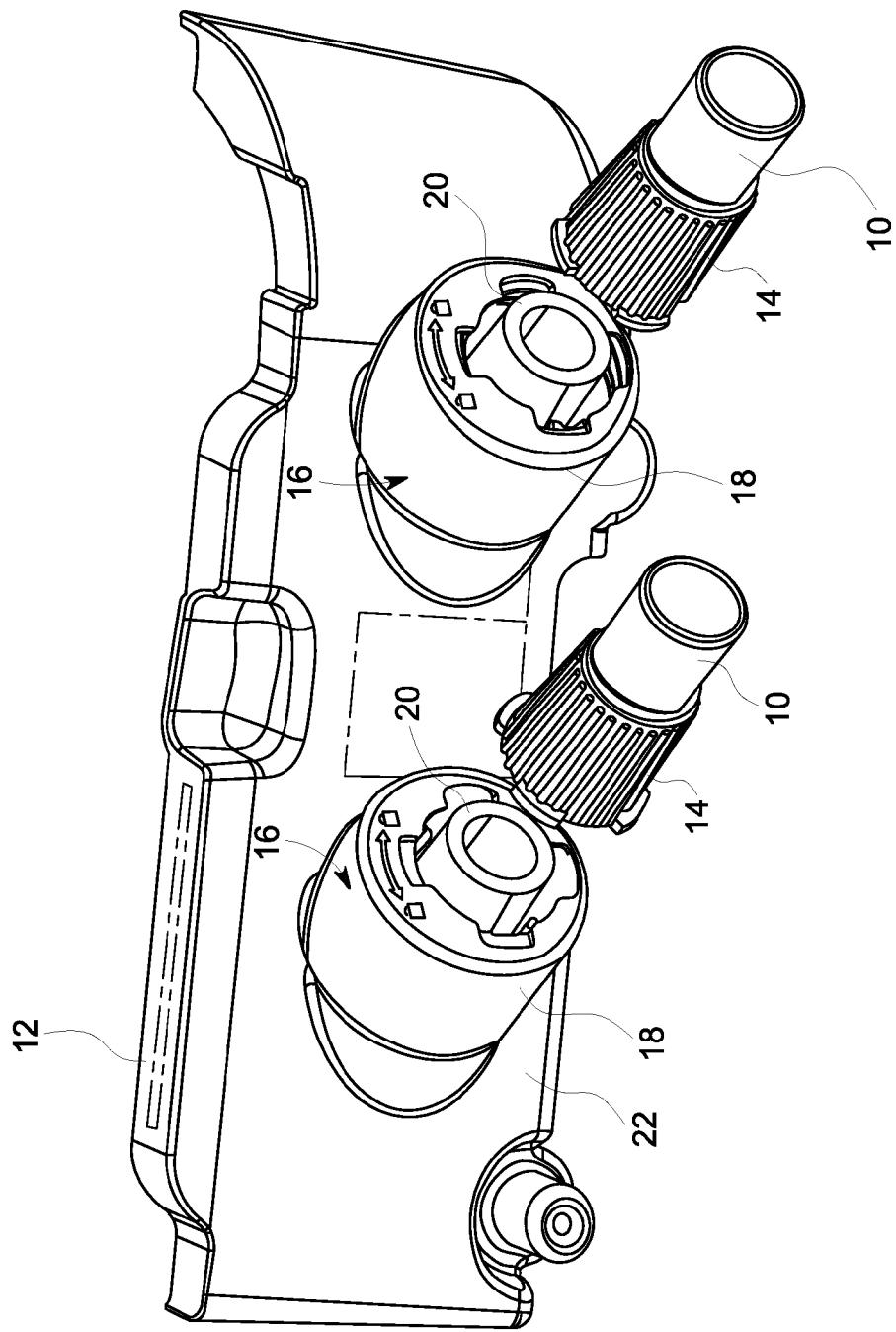
FIG. 2 is a view similar to FIG. 1 with the pair of connectors separated from the corresponding receptacles.

Referring now to FIG. 2, the connector 14 of each of the gas conduits 10 can be separated from the corresponding receptacle 16 such that the gas conduits 10 can be disconnected and replaced as desired. As shown in FIG. 2, the receptacle 16 includes a stationary outer shroud 18 that surrounds a supply port 20 that extends from a face surface 22 of the anesthesia machine 12. The supply port 20 engages the gas conduit 10 to either supply or receive gas from the conduits 10 when the connector 14 is received within the receptacle 16.

Figure 3:
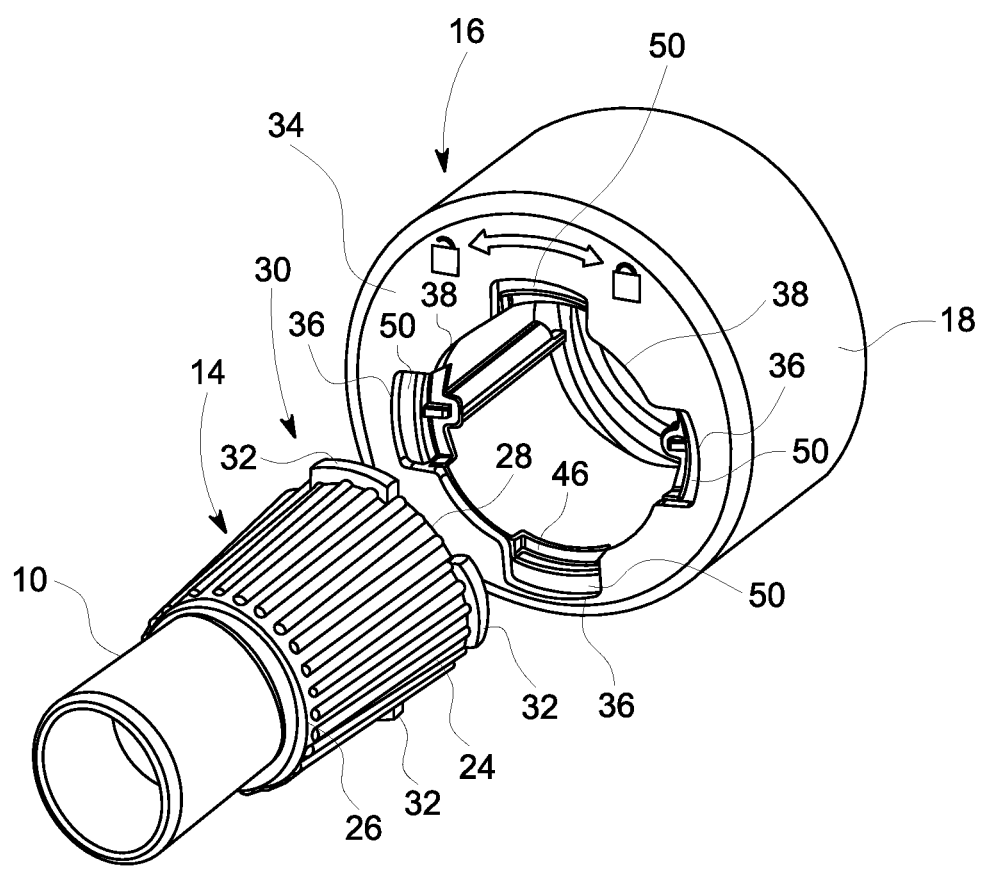
FIG. 3 is a perspective view of the connector and receptacle prior to receipt of the connector in the receptacle.

Referring now to FIG. 3, the connector 14 formed on the gas conduit 10 includes a series of raised gripping ridges 24 formed on a cylindrical outer wall 26. The cylindrical outer wall 26 is securely attached to the gas conduit 10 to provide a point of attachment between the gas conduit 10 and the anesthesia machine.

The distal end 28 of the connector 14 includes a locking arrangement 30. In the embodiment illustrated, the locking arrangement 30 includes a series of spaced retaining tabs 32. In the embodiment illustrated in FIG. 3, four separate retaining tabs 32 are equally positioned along the outer circumference of the outer wall 26 near the distal end 28.

The receptacle 16 formed on the anesthesia machine includes the outer shroud 18. The outer shroud 18 includes a front face surface 34 that includes a series of spaced receiving slots 36 each separated from each other by a series of retaining projections 38. As illustrated in FIG. 3, the size of the receiving slots 36 generally correspond to the size of the retaining tabs 32 formed on the connector 14.

Figure 6:
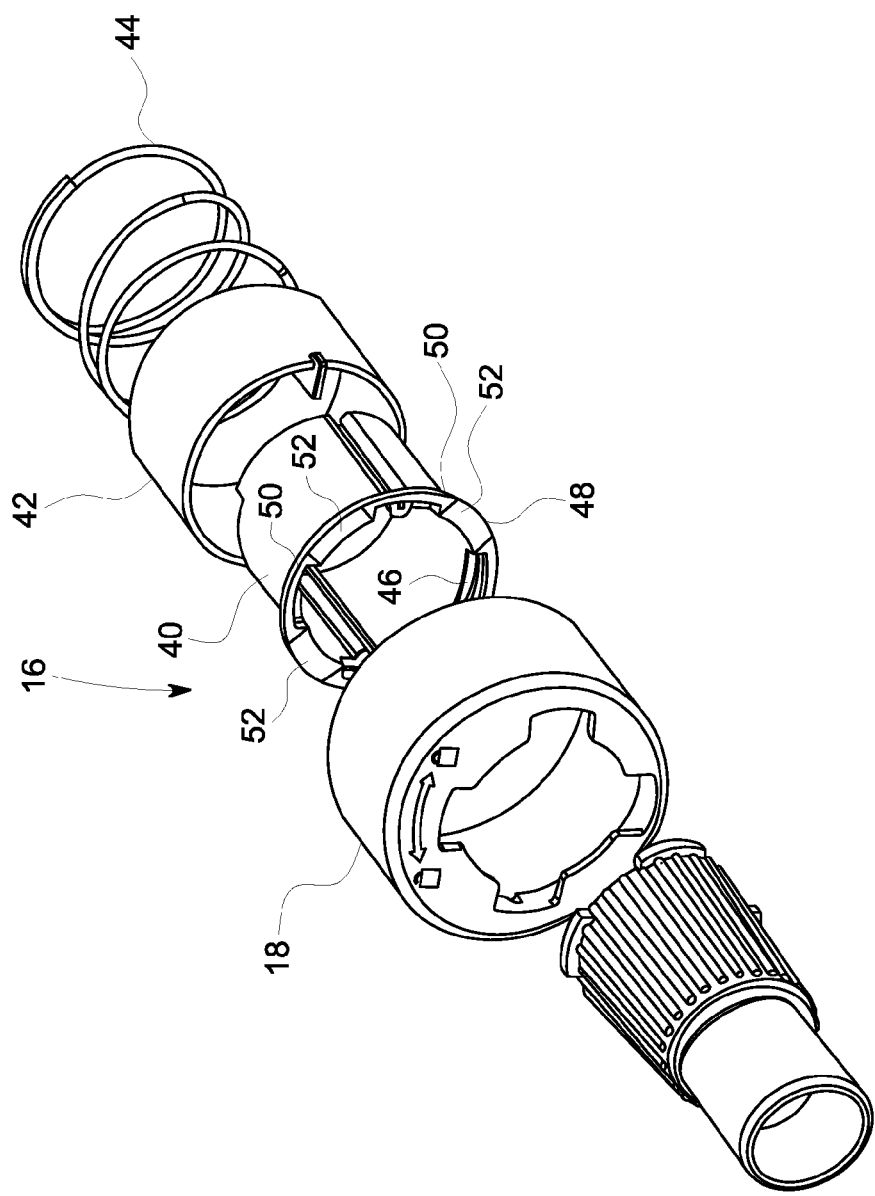
FIG. 6 is an exploded perspective view of the components of the receptacle.

Referring now to FIG. 6, the receptacle 16 of the first embodiment is shown in an exploded view. The receptacle 16 includes a receiving arrangement (31) including the outer shroud 18, a visual indicator shroud 40, a bias ring 42 and a bias spring 44. The bias spring 44 exerts a bias force on the bias ring 42, which in turn exerts a bias force on the visual indicating shroud 40.

Referring now to FIGS. 3 and 6, the visual indicating shroud 40 includes a series of receiving slots 46 that are each aligned with one of the receiving slot 36 formed in the outer shroud 18. The receiving slots 46 are each sized to receive one of the retaining tabs 32 formed on the connector 14. The receiving slots 46 are each recessed from an outer rim 48.

Referring back to FIG. 6, the outer rim 48 includes a series of first portions 50 and second portions 52 that are alternately spaced around the generally circular outer rim 48. In the embodiment illustrated in FIG. 6, the first portion 50 is of a first color, red, and the second portion 52 is of a second color, green. Although red and green are described as being the colors for the first and second portions 50, 52, it should be understood that other colors could be utilized while operating within the scope of the present disclosure.

Referring back to FIG. 3, before the connector 14 is inserted into the receptacle 16, the first portion 50 of the visual indicating shroud 40 is visible through each of the receiving slots 36. Since the first portion 50 is red, the user is presented with a visual indication that the connector 14 is not properly inserted into the receptacle 16.

Figure 4:
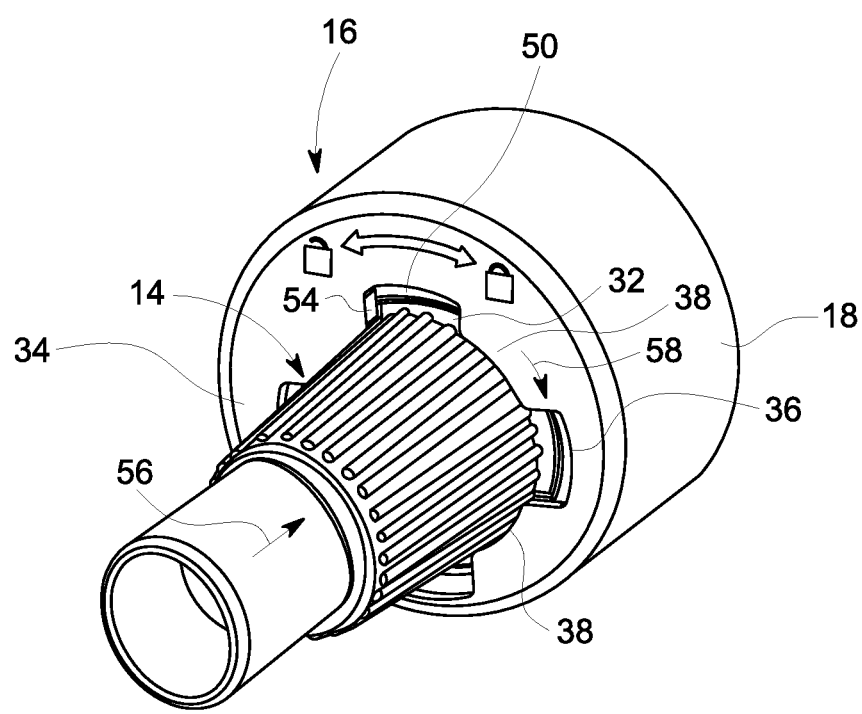
FIG. 4 is a perspective view illustrating the initial receipt of the connector within the receptacle.

Referring now to FIG. 4, when the connector 14 is initially inserted into the receptacle 16, the retaining tabs 32 are received within the receiving slots 46 of the visual indicating shroud. When the connector 14 is received as shown in FIG. 4, an outer portion of the first portion 50 of the visual indicating shroud is still visible to the user. Thus, the user views the red color of the first portion 50 when the connector 14 is first inserted into the receptacle 16.

Once the retaining tabs 32 of the connector 14 are received in each of the receiving slots 36, the connector 14 is depressed against the bias force created by the bias spring until the retaining tabs 32 are recessed enough to extend past the front wall 54 of the outer shroud 18. The movement of the connector 14 in the direction shown by arrow 56 causes the visual indicating shroud 40 and the bias ring 42 to compress the bias spring 44, which allows the visual indicating shroud 40 to move inwardly. Once the bias spring 44 has been compressed, the connector 14 is rotated in the clockwise direction, as indicated by arrow 58.

Figure 5:
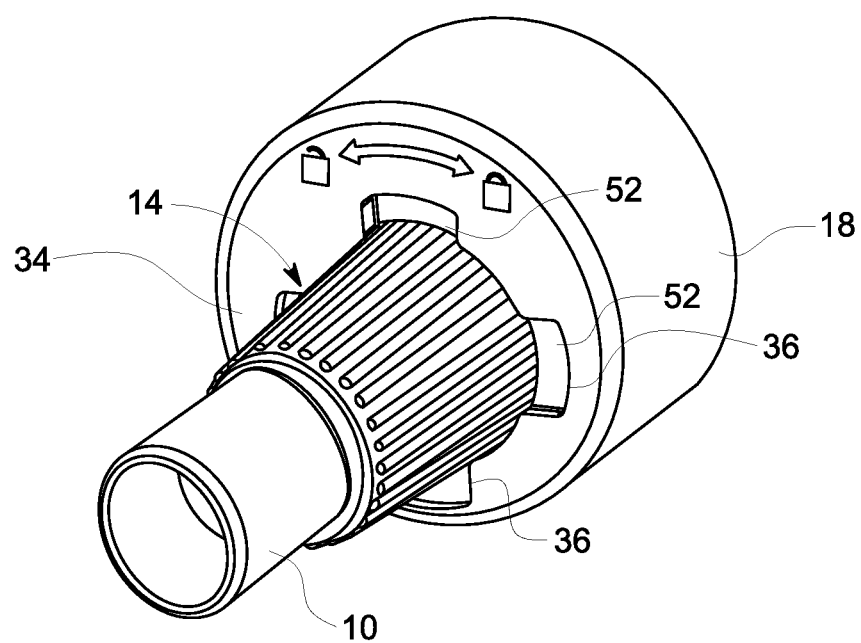
FIG. 5 is a perspective view illustrating the rotation of the connector relative to the receptacle and into the locked position.

Rotation of the connector 14 in the clockwise direction causes the retaining tabs 32 to be entrapped beneath the retaining projections 38 formed on the face surface 34. Referring now to FIG. 5, once the connector 14 has been rotated, the second portion 52 of the visual indicating shroud 40 is visible through the receiving slots 36. As described previously, the second portion 52 has a second color, green, which is visible and indicates to the user that the connector has been positively retained within the receptacle. In this manner, the user can quickly determine that the connector has been properly attached to the receptacle and that a fluid tight communication is achieved between the gas conduit 10 and the anesthesia machine.

As illustrated in FIG. 5, the front face surface 34 of the outer shroud 18 includes a printed arrow and locking icons to illustrate to the user which direction the connector 14 needs to be rotated to lock and unlock the connector from within the receptacle 16. As described above, the visual indicating shroud 40 shown in FIG. 6 is formed having two different colors to visually indicate to the user when the connector has been properly received within the receptacle. In the preferred embodiment, the first portion 50 and the second portion 52 are colored red and green, which are commonly used colors to indicate a proper connection and an improper connection. However, other colors could be utilized while operating within the scope of the present disclosure.

Additionally, although the illustrated embodiment requires rotation of the connector 14 in the clockwise direction to enter the locked condition, the orientation of the connector and receptacle could be reversed such that counter-clockwise rotation would create the locked condition. Further, the connector and receptacle could be configured such that rotation of the connector in either direction could create the locked condition. In such an embodiment, the first and second colored portions would be located appropriately on the visual indicating shroud 40 to indicate that the connector has been positively retained within the receptacle.

Figure 7:
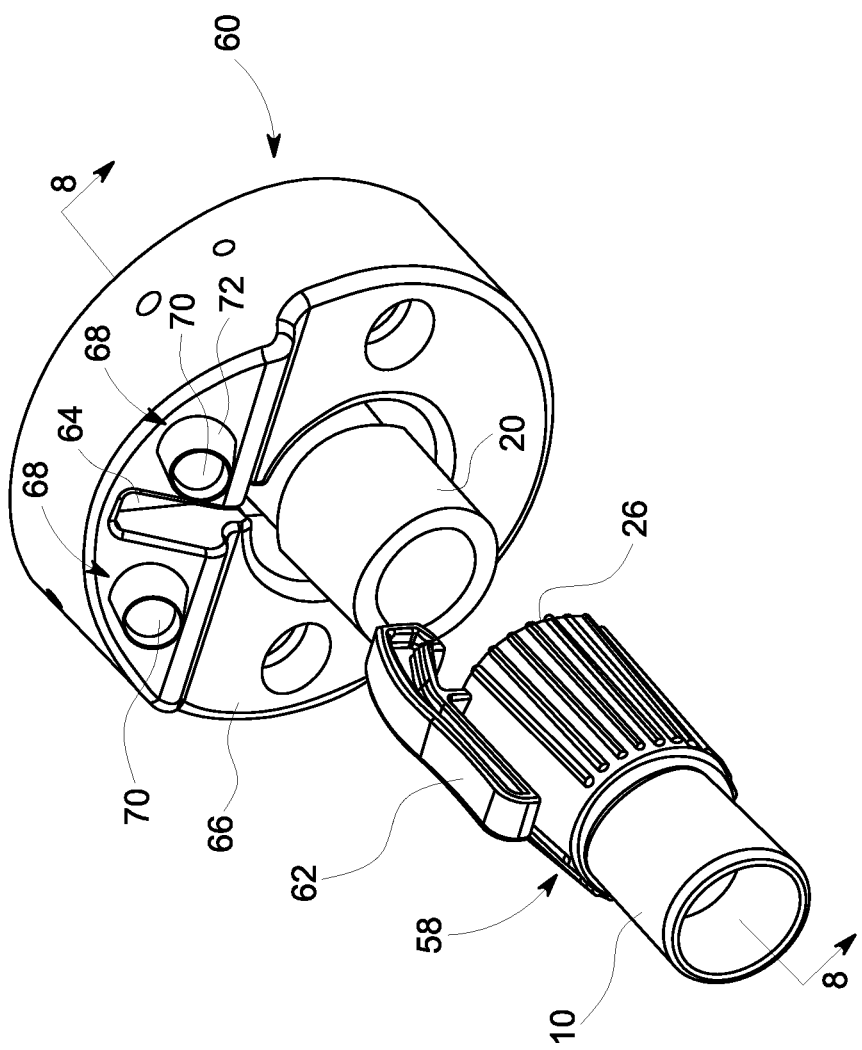
FIG. 7 is a perspective view of a second embodiment of the connector arrangement with the connector on the gas conduit separated from the receptacle.

FIG. 7 illustrates a second embodiment of the connector arrangement of the present disclosure. In the embodiment of FIG. 7, the gas conduit 10 includes a connector 58 having an alternate configuration. Likewise, the anesthesia machine includes an alternate receptacle 60 in accordance with the second embodiment. The receptacle 60 surrounds the supply port 20 and acts as a receptacle for the connector 58 to positively retain the connector 58 while creating the fluid communication between the gas conduit 10 and the supply port 20.

In the embodiment shown in FIG. 7, the connector 58 includes a locking arrangement formed by a latch 62 that extends from the outer wall 26 of the connector 58. The latch 62 is received within an access opening 64 formed in the outer shroud 66 of the receptacle 60. The outer shroud 66 further includes a pair of visual indicators 68 that provide a visual indication of the proper connection of the connector 58 to the receptacle 60. In the embodiment illustrated in FIG. 7, the visual indicators 68 include a pair of light emitting diodes (LEDs) 70 that are each contained within an outer shroud 72. Although LEDs 70 are shown, it should be understood that the visual indicator could be another type of illumination light while operating within the scope of the present disclosure.

Figure 8:
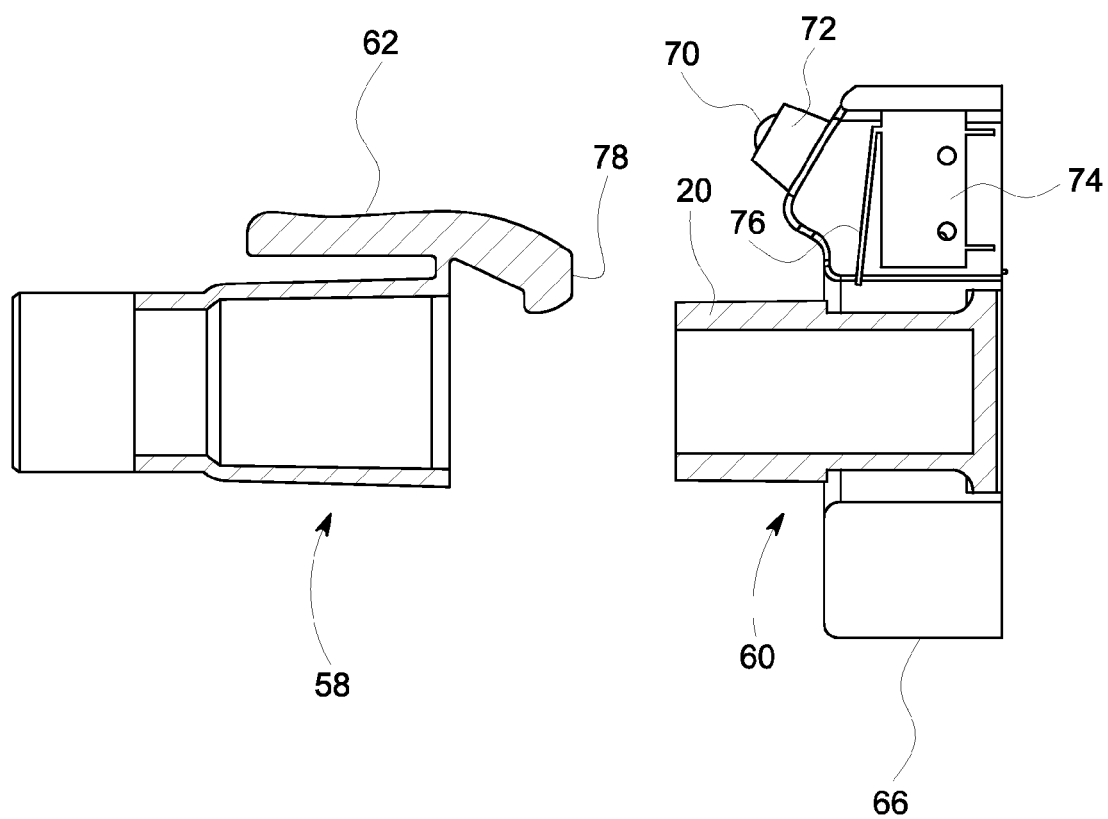
FIG. 8 is a section view taken along line 8-8 of FIG. 7.

Referring now to FIG. 8, the pair of LEDs 70 are each connected to an activation switch 74 contained within the outer shroud 66. The activation switch 74 is connected to a supply of power and includes a movable switch arm 76. When the switch arm 76 is moved from the resting position shown in FIG. 8 to the depressed position of FIG. 10, the switch arm 76 closes a pair of contacts within the activation switch 74, which results in power being applied to the LED, thereby resulting in illumination of the LED 70. However, when the switch arm 76 is in the position shown in FIG. 8, the switch contacts are open and no power is applied to the LED 70 and the LED 70 is not illuminated.

Figure 9:
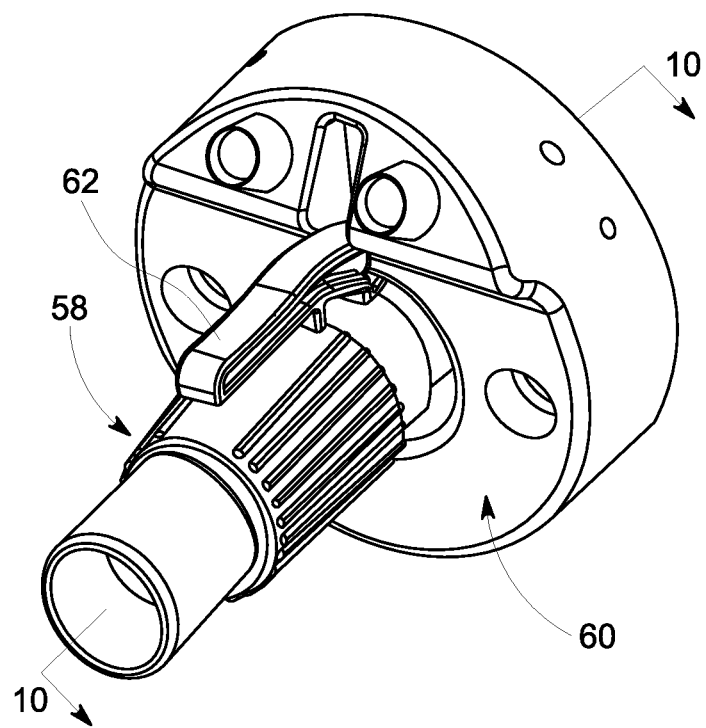
FIG. 9 is a perspective view of the engagement between the connector and receptacle.
Figure 10:
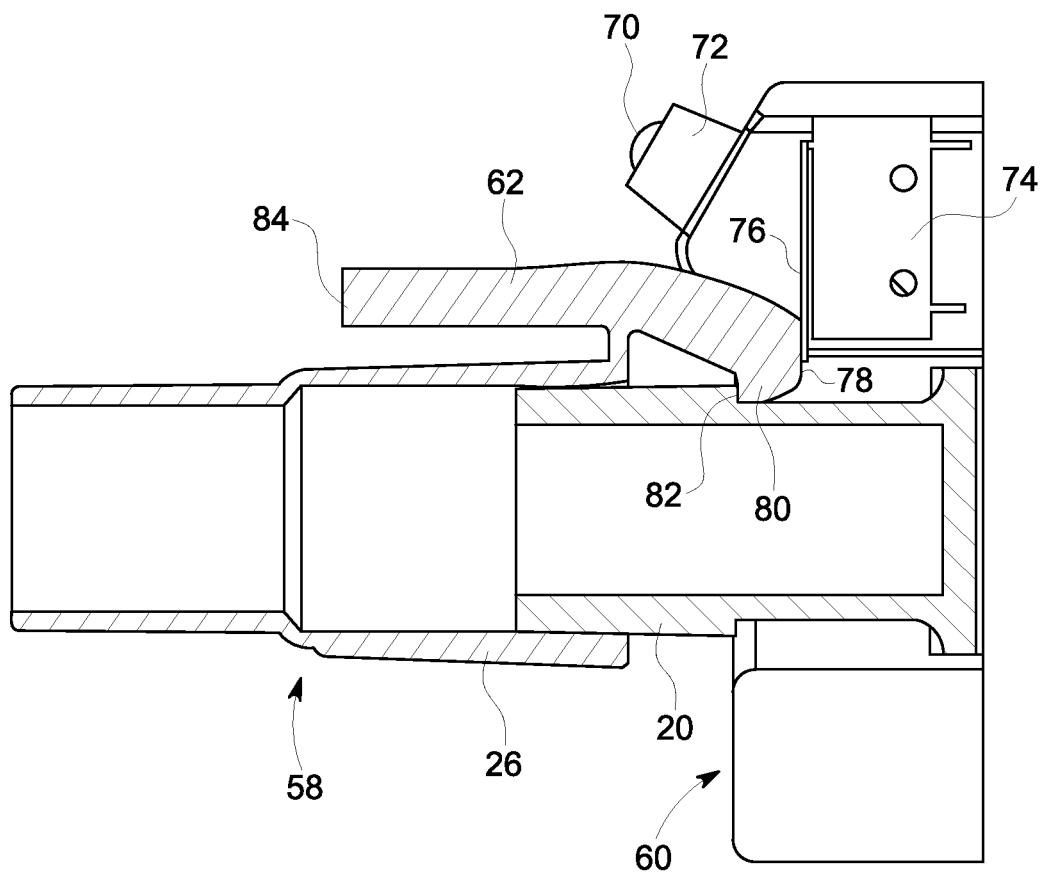
FIG. 10 is a section view taken along line 10-10 of FIG. 9.

Referring now to FIGS. 9 and 10, when the connector 58 is inserted into the receptacle 60, an outer end 78 of the latch 62 contacts the switch arm 76 to move the switch arm 76 to the depressed position, as best shown in FIG. 10. When the switch arm 76 of the activation switch 74 has been depressed as shown in FIG. 10, the activation switch 74 provides electric power to the LED 70, which in turn activates the LED 70. In the latched condition shown in FIG. 10, the locking end 80 of the latch 62 engages shoulder 82 formed on the supply port 20. In this latched condition, the outer wall 26 surrounds the supply port 20 and the connector 58 is positively retained within the receptacle 60.

When it is desired to remove the connector 58 from the receptacle 60, the outer end 84 of the latch 62 is depressed, which causes the locking end 80 to move upward away from the shoulder 82, as illustrated in FIG. 10. Once the locking end 80 has been elevated, the connector 58 can simply be removed from the receptacle 60.

As can be understood in the second embodiment illustrated in FIGS. 7-10, the visual indicators 68 provide a visual indication to the user when a positive connection is made between the connector 58 and the receptacle 60. Although a pair of LEDs 70 are shown in the embodiment illustrated, it should be understood that a single LED or other types of light emitting devices could be utilized while operating within the scope of the present disclosure.

Figure 11:
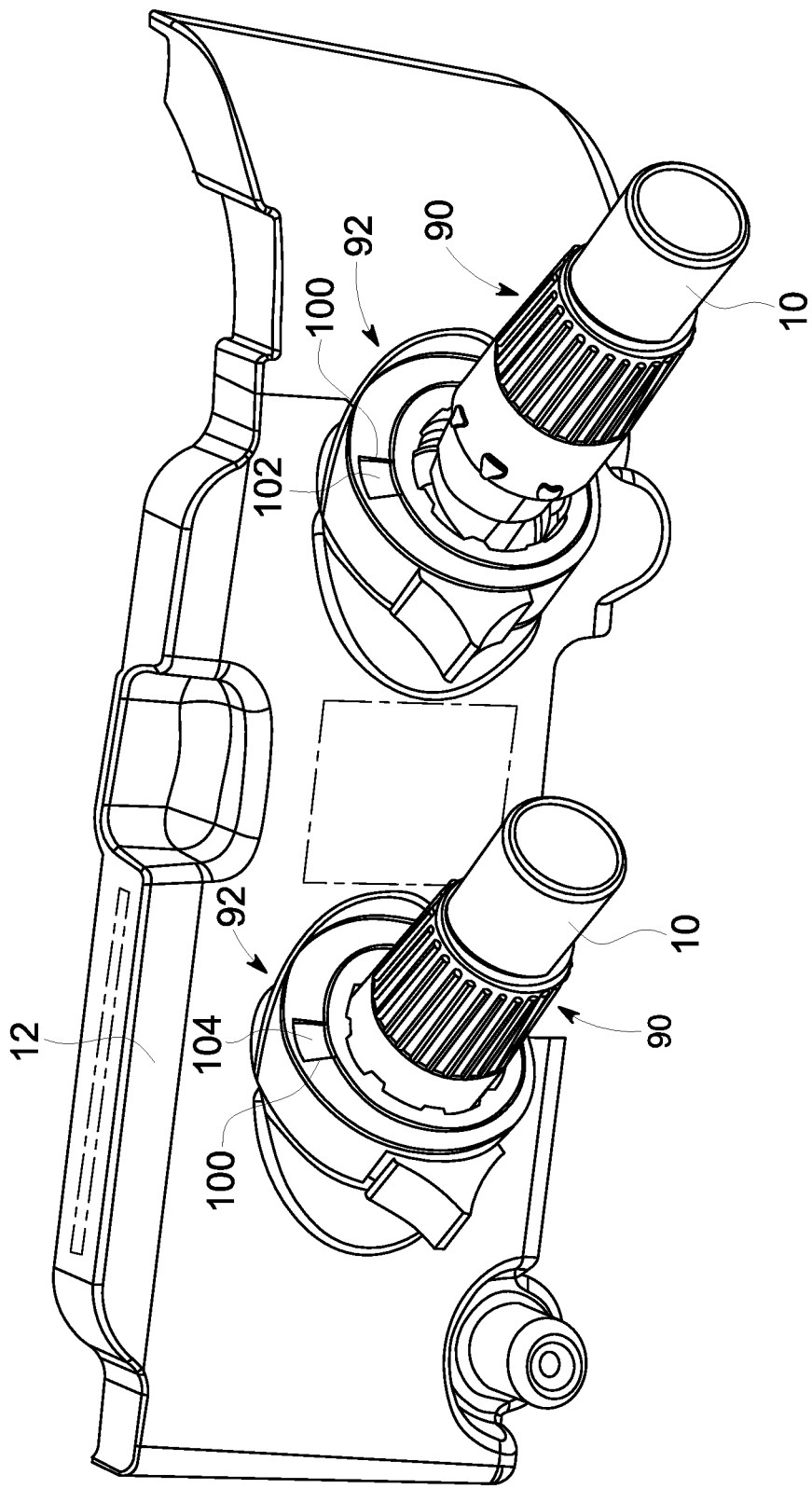
FIG. 11 is a front perspective view of a third embodiment of the connector arrangement.

Referring now to FIG. 11, there shown is yet a third embodiment of the connector arrangement of the present disclosure. In the embodiment shown in FIG. 11, the pair of gas conduits 10 each include a unique connector 90 that is received within a receptacle 92 formed as part of the anesthesia machine 12. In the embodiment shown in FIG. 11, the leftmost connector is shown in its positively retained condition while the rightmost connector 90 is separated from the receptacle 92.

Figure 12:
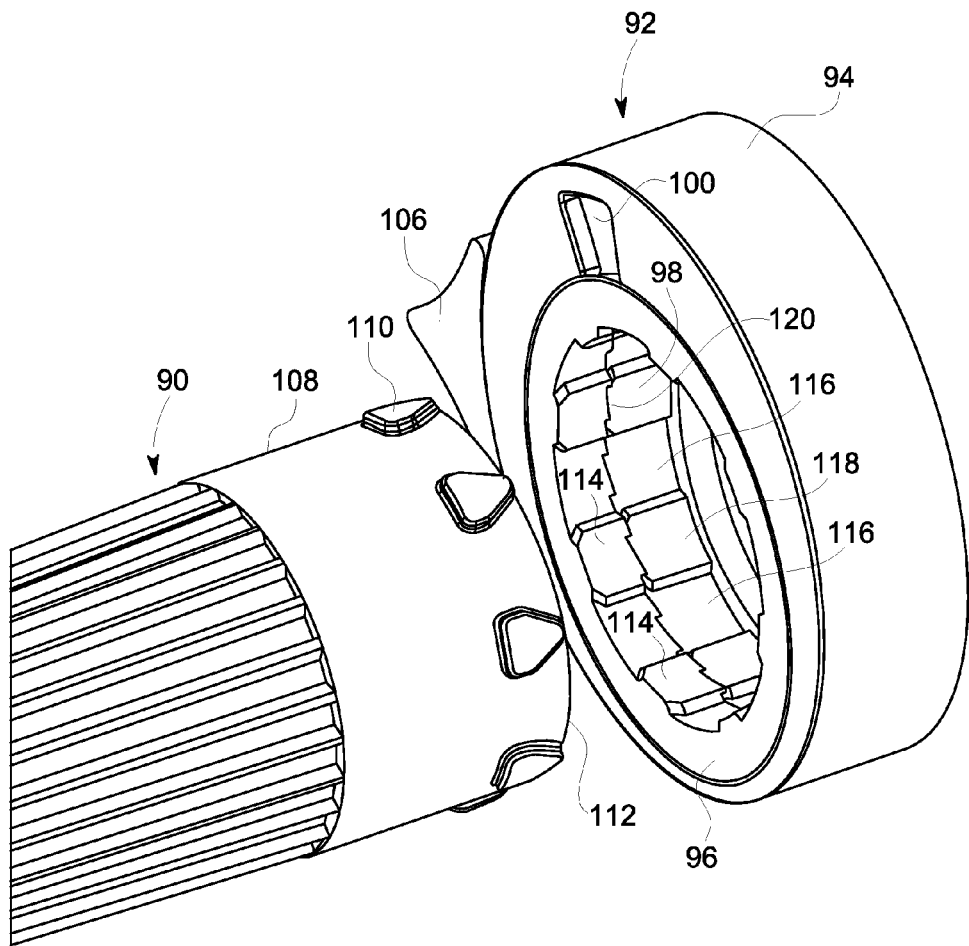
FIG. 12 is a front perspective view illustrating the insertion of the connector into the receptacle of the third embodiment.

Referring now to FIG. 12, the receptacle 92 includes an outer shroud 94 that surrounds a retaining ring 96 and a visual indicator shroud 98. As illustrated in FIG. 12, the outer shroud 94 includes a viewing window 100 that allows a user to view a portion of the visual indicator shroud 98. The visual indicator shroud 98 includes both a first portion and a second portion that have different colors, such as red and green as described in the first embodiment previously discussed.

Referring back to FIG. 11, when the connector 90 is inserted as shown in FIG. 11, a first portion 102 of the visual indicator shroud is visible through the viewing window 100. When the connector 90 is separated from the receptacle, as shown in the rightmost embodiment, a first portion 102 is visible through the viewing window 100. As discussed previously, the first portion 102 is preferably colored red to indicate no connection while the second portion 104 is colored green to indicate a proper connection.

Referring back to FIG. 12, a release handle 106 is connected to the visual indicating shroud 98 and is sized to receive the thumb of a user. The release handle 106 allows the user to release the connector 90 from within the receptacle 92, as will be described in detail below.

Referring back to FIG. 12, the connector 90 includes an engagement end 108 having a series of retaining tabs 110 positioned near the distal end 112. The spacing between the retaining tabs 110 corresponds to the spacing between a series of locking tabs 114 formed on the retaining ring 96.

During initial connection of the connector 90 to the receptacle 92, the series of retaining tabs 110 are aligned with the open spaces between the locking tabs 114 of the retaining ring 96. The connector 90 is moved inwardly relative to the stationary outer shroud 94 until the retaining tabs 110 are received within the open receiving slots 116 formed in the visual indicator shroud 98. The receiving slots 116 are spaced between a series of engagement tabs 118 that project radially outward and are flush with the locking tabs 114. As can be seen in FIG. 12, the retaining ring 96 and the visual indicating shroud 98 interact with each other along a serrated contact surface 120. The serrated contact surface 120 allows the two rings to rotate in only one direction relative to each other.

Figure 13:
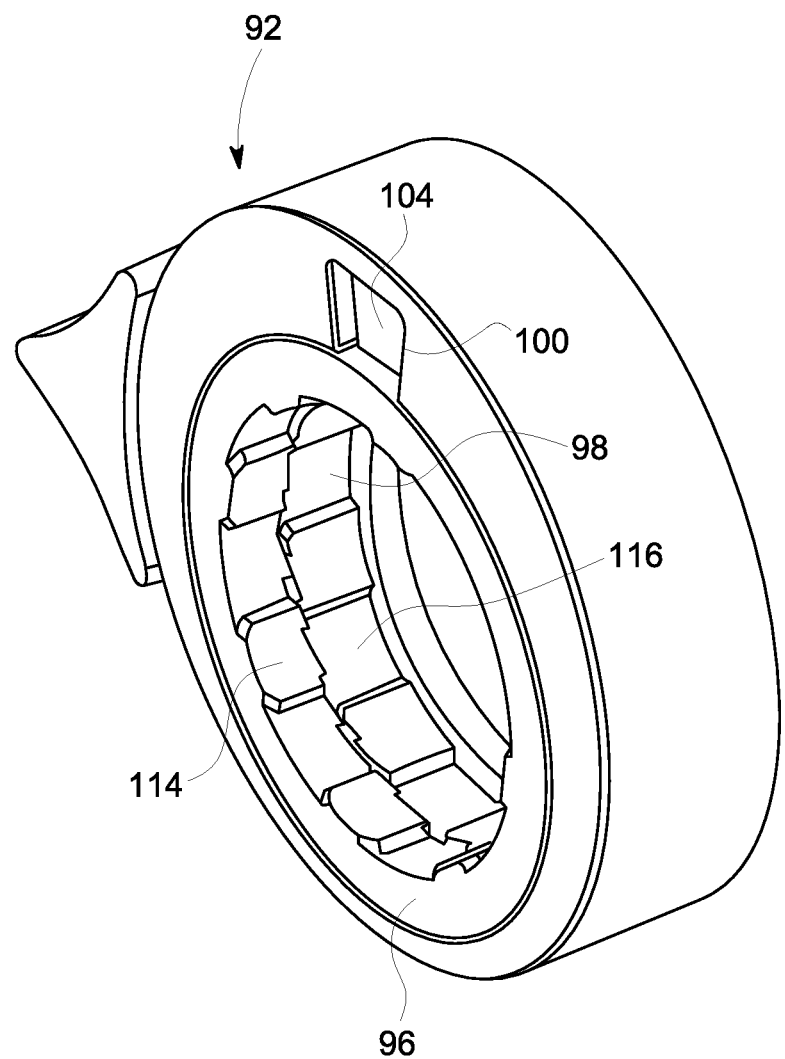
FIG. 13 is a front perspective view of the receptacle in the locking condition.

Once the retaining tabs 110 are received within the receiving slots 116, the entire connector 90 is rotated in the clockwise direction, which causes the retaining ring 96 and the visual indicator shroud 98 to rotate into the condition shown in FIG. 13. Although the connector is not shown in FIG. 13, each of the retaining tabs 110 are positioned within the receiving slot 116 and thus positioned behind the locking tabs 114 in this rotated condition. In this condition, the connector is securely held within the receptacle 92 and the second portion 104 of the visual indicator shroud 98 is visible through the viewing window 100. As described previously, the second portion is preferably colored green such that the second portion 104 indicates a proper connection between the connector and the receptacle.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. A connector arrangement that connects a gas conduit to a gas supply device, comprising:
   a connector attached to the gas conduit, the connector comprising a plurality of spaced retaining tabs;
   a receptacle formed on the gas supply device and sized to receive the connector and comprising a plurality of receiving slots spaced from each other by a plurality of retaining projections, the receiving slots configured to receive the retaining tabs, and the connector configured to rotate such that the retaining tabs rotate behind the retaining projections to retain the connector within the receptacle; and a visual indicator associated with the receptacle, the visual indicator comprising a visual indicator shroud within the receptacle, the visual indicator shroud configured to rotate with the connector, and the visual indicator shroud having an outer surface, wherein the visual indicator has a first state that provides a visual indication of when the retaining tabs are not rotated behind the retaining projections, and a second state that provides a visual indication of when the retaining tabs are fully rotated behind the retaining projections, wherein rotation of the connector transitions the visual indicator from the first state to the second state, wherein the second state indicates a fluid tight communication is achieved between the gas conduit and the gas supply device, and wherein a first portion of the outer surface of the visual indicator shroud is visible through at least one receiving slot of the receptacle in the first state and is not visible in the second state, and a second portion of the outer surface of the visual indicator shroud, different than the first portion, is visible through the at least one receiving slot of the receptacle in the second state and is not visible in the first state.

2. The connector arrangement of claim 1 wherein the first portion of the indicator shroud is of a first color and the second portion is of a second color.

3. The connector arrangement of claim 1 wherein the visual indicator shroud is spring biased.

4. The connector arrangement of claim 3, wherein the spring biased visual indicator shroud exerts a bias force on the retaining tabs when the connector is received and retained in the receptacle.

5. The connector arrangement of claim 1 wherein the retaining tabs engage a series of locking tabs formed on a retaining ring of the receptacle.

6. The connector arrangement of claim 5 wherein the visual indicator shroud is spring biased.

7. The connector arrangement of claim 1 wherein the visual indicator changes from the first state to the second state once the connector is positively received and retained in the receptacle.

8. The connector arrangement of claim 1, wherein the visual indicator shroud comprises an outer rim comprising the first portion and the second portion.

9. A connector arrangement that connects a gas conduit of a breathing circuit to an anesthesia machine, comprising:

a connector attached to the gas conduit, the connector including a locking arrangement, the locking arrangement comprising a retaining tab;

a receptacle formed on the anesthesia machine and having a receiving arrangement for positively receiving and retaining the locking arrangement of the connector, the receiving arrangement comprising a receiving slot adjacent a retaining projection; and a visual indicator associated with the receptacle, the visual indicator comprising a visual indicator shroud positioned within the receptacle and comprising an outer rim at least partially visible through the receiving slot from within the receptacle, the visual indicator shroud configured to receive the connector, wherein the visual indicator changes state to provide a visual indication of when the locking arrangement is fully locked with the receiving arrangement, the locking arrangement fully locked with the receiving arrangement when the retaining tab is completely rotated behind the retaining projection, wherein a portion of the outer rim is visible when the locking mechanism is fully locked with the receiving mechanism and the portion is not visible when the locking mechanism is not locked with the receiving mechanism, and wherein a fluid tight communication is achieved between the gas conduit and the anesthesia machine when the locking mechanism is fully locked with the receiving mechanism.

10. The connector arrangement of claim 9 wherein the visual indicator changes from a first state to a second state once there is a secure connection between the connector and the receptacle.

11. The connector arrangement of claim 9 wherein the visual indicator gradually transitions from a first state to a second state as the connector is positively received and retained in the receptacle.

12. The connector arrangement of claim 9, wherein the locking arrangement comprises a plurality of spaced retaining tabs, the receiving arrangement comprises a plurality of receiving slots spaced from each other by a plurality of retaining projections, the locking arrangement fully locks with the receiving arrangement by fully rotating the retaining tabs behind the retaining projections, and wherein the plurality of spaced retaining tabs includes the retaining tab, the plurality of receiving slots includes the receiving slot, and the plurality of retaining projections includes the retaining projection.

13. The connector arrangement of claim 12, wherein the connector is configured to rotate to fully lock the locking arrangement with the receiving arrangement and the visual indicator shroud is configured to rotate with the connector.

* * * * *